(12) United States Patent
Vaillancourt et al.

(10) Patent No.: US 8,065,773 B2
(45) Date of Patent: Nov. 29, 2011

(54) MICROBIAL SCRUB BRUSH

(75) Inventors: Michael J. Vaillancourt, Chester, NJ (US); Marshall Kerr, Oceanside, CA (US)

(73) Assignee: Bard Access Systems, Inc., Salt Lake City, UT (US)

( * ) Notice: Subject to any disclaimer, the term of this patent is extended or adjusted under 35 U.S.C. 154(b) by 1136 days.

(21) Appl. No.: 11/732,075

(22) Filed: Apr. 2, 2007

(65) Prior Publication Data

US 2008/0235888 A1    Oct. 2, 2008

(51) Int. Cl.
*B08B 9/00*    (2006.01)
(52) U.S. Cl. ............... 15/104.94; 15/104.93; 15/160; 604/267
(58) Field of Classification Search .......... 15/104.04, 15/104.05, 104.92, 160, 104.93; 604/265, 604/267
See application file for complete search history.

(56) References Cited

U.S. PATENT DOCUMENTS

| | | | |
|---|---|---|---|
| 2,814,818 A * | 12/1957 | Birse ..................... | 15/143.1 |
| 3,396,727 A | 8/1968 | Mount | |
| 3,450,129 A | 6/1969 | Brewer | |
| 3,860,348 A | 1/1975 | Doyle | |
| 3,915,806 A | 10/1975 | Horlach | |
| 3,961,629 A | 6/1976 | Richter et al. | |
| 4,340,052 A | 7/1982 | Dennehey et al. | |
| 4,354,490 A | 10/1982 | Rogers | |
| 4,417,890 A | 11/1983 | Dennehey et al. | |
| 4,432,259 A | 2/1984 | Werth, Jr. | |
| 4,432,764 A | 2/1984 | Lopez | |
| 4,440,207 A | 4/1984 | Genatempo et al. | |
| 4,551,146 A | 11/1985 | Rogers | |
| 4,624,664 A | 11/1986 | Peluso et al. | |
| 4,734,950 A | 4/1988 | Schenke et al. | |
| 4,752,983 A | 6/1988 | Grieshaber | |
| 4,830,674 A | 5/1989 | Kaufman | |
| 4,862,549 A | 9/1989 | Criswell | |
| 4,872,235 A | 10/1989 | Nielsen | |
| 4,886,388 A * | 12/1989 | Gulker et al. ........ | 401/148 |
| 4,893,956 A | 1/1990 | Wojcik et al. | |
| 4,919,837 A | 4/1990 | Gluck | |
| 4,989,733 A | 2/1991 | Patry | |
| 5,049,139 A | 9/1991 | Gilchrist | |
| 5,180,061 A | 1/1993 | Khan et al. | |
| 5,195,957 A | 3/1993 | Tollini | |

(Continued)

FOREIGN PATENT DOCUMENTS

DE    103 35 794 A1    10/2005

(Continued)

OTHER PUBLICATIONS

EP08250832 filed Mar. 12, 2008 EP Search Report dated Aug. 15, 2008.

(Continued)

*Primary Examiner* — Shay L Karls
(74) *Attorney, Agent, or Firm* — Rutan & Tucker, LLP

(57) ABSTRACT

The microbial scrub brush employs an insert of foam material that is impregnated with an anti-bacterial disinfectant that is housed within a housing of alcohol compatible material and sealed over by a removable lid. The insert is maintained in sterile condition until ready for use. After the removal of the lid, the insert of foam material is moved over the end of a female luer and rotated in order to clean the outer surface of the luer as well as the interior of the luer.

13 Claims, 3 Drawing Sheets

U.S. PATENT DOCUMENTS

| | | | |
|---|---|---|---|
| 5,242,425 A | 9/1993 | White et al. |
| 5,274,874 A | 1/1994 | Cercone et al. |
| 5,308,406 A | 5/1994 | Wallock et al. |
| 5,330,235 A | 7/1994 | Wagner et al. |
| 5,368,049 A | 11/1994 | Raman et al. |
| 5,372,429 A | 12/1994 | Beaver, Jr. et al. |
| 5,471,706 A | 12/1995 | Wallock et al. |
| 5,536,258 A | 7/1996 | Folden |
| 5,554,135 A | 9/1996 | Menyhay |
| 5,719,113 A | 2/1998 | Fendler et al. |
| 5,722,537 A | 3/1998 | Sigler |
| 5,743,892 A | 4/1998 | Loh et al. |
| 5,763,412 A | 6/1998 | Khan et al. |
| 5,776,430 A | 7/1998 | Osborne et al. |
| 5,782,808 A | 7/1998 | Folden |
| 5,792,120 A | 8/1998 | Menyhay |
| 5,829,976 A | 11/1998 | Green |
| 5,830,488 A | 11/1998 | Suzuki et al. |
| 5,894,015 A | 4/1999 | Rechtin |
| 5,906,808 A | 5/1999 | Osborne et al. |
| 5,980,925 A | 11/1999 | Jampani et al. |
| 6,045,539 A | 4/2000 | Menyhay |
| 6,045,623 A | 4/2000 | Cannon |
| 6,086,275 A | 7/2000 | King |
| 6,096,701 A | 8/2000 | Mondin et al. |
| 6,108,847 A | 8/2000 | Cueman et al. |
| 6,110,292 A | 8/2000 | Jewett et al. |
| 6,116,468 A | 9/2000 | Nilson |
| 6,130,196 A | 10/2000 | Mondin et al. |
| 6,143,025 A | 11/2000 | Stobie et al. |
| 6,152,913 A | 11/2000 | Feith et al. |
| 6,250,315 B1 | 6/2001 | Ernster |
| 6,254,550 B1 | 7/2001 | McNamara et al. |
| 6,289,547 B1 | 9/2001 | Narula et al. |
| 6,299,520 B1 | 10/2001 | Cheyne, III |
| 6,357,947 B1 | 3/2002 | Mark |
| 6,387,865 B1 | 5/2002 | Mondin et al. |
| 6,387,866 B1 | 5/2002 | Mondin et al. |
| 6,395,697 B1 | 5/2002 | Cheung et al. |
| 6,432,213 B2 | 8/2002 | Wang et al. |
| 6,447,446 B1 | 9/2002 | Smith et al. |
| 6,472,356 B2 | 10/2002 | Narula |
| 6,488,942 B1 | 12/2002 | Ingemann |
| 6,508,602 B1 | 1/2003 | Gruenbacher et al. |
| 6,564,415 B1 | 5/2003 | Katakura et al. |
| 6,589,212 B1 * | 7/2003 | Navis ..................... 604/164.01 |
| 6,617,294 B2 | 9/2003 | Narula et al. |
| 6,669,387 B2 | 12/2003 | Gruenbacher et al. |
| 6,708,363 B2 | 3/2004 | Larsen |
| 6,726,386 B1 | 4/2004 | Gruenbacher et al. |
| 6,745,425 B1 | 6/2004 | Tope |
| 6,821,043 B2 | 11/2004 | Teh |
| 6,855,678 B2 | 2/2005 | Whiteley |
| 6,911,025 B2 | 6/2005 | Miyahara |
| 6,991,527 B2 | 1/2006 | Linzell |
| 7,083,605 B2 | 8/2006 | Miyahara |
| 7,108,440 B1 | 9/2006 | Gruenbacher et al. |
| 7,163,914 B2 | 1/2007 | Gluck et al. |
| 7,179,007 B2 | 2/2007 | Wong et al. |
| 7,199,090 B2 | 4/2007 | Koivisto et al. |
| 7,282,186 B2 | 10/2007 | Lake, Jr. et al. |
| 7,338,927 B2 | 3/2008 | Shapiro |
| 7,452,349 B2 | 11/2008 | Miyahara |
| 7,488,757 B2 | 2/2009 | Hoang et al. |
| 7,513,957 B2 | 4/2009 | Condliff |
| 7,537,779 B2 | 5/2009 | Modak et al. |
| D596,308 S | 7/2009 | Fisher |
| 7,560,422 B2 | 7/2009 | Shapiro |
| D607,325 S | 1/2010 | Rogers et al. |
| 2001/0031221 A1 | 10/2001 | Wu et al. |
| 2001/0031721 A1 | 10/2001 | Webb et al. |
| 2001/0032659 A1 | 10/2001 | Wang et al. |
| 2002/0002984 A1 | 1/2002 | Loy |
| 2002/0022660 A1 | 2/2002 | Jampani et al. |
| 2002/0062147 A1 | 5/2002 | Yang |
| 2003/0019767 A1 | 1/2003 | Cabrera |
| 2003/0144647 A1 | 7/2003 | Miyahara |
| 2003/0147925 A1 | 8/2003 | Sawan et al. |
| 2003/0156884 A1 | 8/2003 | Teh |
| 2003/0164175 A1 | 9/2003 | Linzell |
| 2003/0211066 A1 | 11/2003 | Scholz et al. |
| 2003/0213501 A1 | 11/2003 | Thomson et al. |
| 2003/0217423 A1 | 11/2003 | Larsen |
| 2004/0052831 A1 | 3/2004 | Modak et al. |
| 2004/0111078 A1 | 6/2004 | Miyahara |
| 2004/0214785 A1 | 10/2004 | Dees et al. |
| 2004/0230162 A1 | 11/2004 | Tan |
| 2004/0237235 A1 | 12/2004 | Visioli et al. |
| 2004/0258560 A1 | 12/2004 | Lake et al. |
| 2005/0081888 A1 | 4/2005 | Pung et al. |
| 2005/0124970 A1 | 6/2005 | Kunin et al. |
| 2005/0171489 A1 | 8/2005 | Weaver et al. |
| 2005/0177964 A1 | 8/2005 | Cisneros |
| 2005/0201812 A1 | 9/2005 | Wong et al. |
| 2005/0214185 A1 | 9/2005 | Castaneda |
| 2005/0215461 A1 | 9/2005 | Gluck et al. |
| 2005/0222542 A1 | 10/2005 | Burkholz et al. |
| 2005/0241088 A1 | 11/2005 | Brunner et al. |
| 2005/0241089 A1 | 11/2005 | Brunner et al. |
| 2005/0282727 A1 | 12/2005 | Shapiro |
| 2006/0003082 A1 | 1/2006 | Marumo et al. |
| 2006/0030827 A1 | 2/2006 | Raulerson et al. |
| 2006/0048313 A1 * | 3/2006 | Yamaki ..................... 15/21.1 |
| 2006/0102200 A1 | 5/2006 | Esquenet et al. |
| 2006/0189961 A1 | 8/2006 | Miyahara |
| 2006/0281663 A1 | 12/2006 | Asmus |
| 2007/0033753 A1 | 2/2007 | Kritzler |
| 2007/0065388 A1 | 3/2007 | Miyamoto et al. |
| 2007/0112333 A1 | 5/2007 | Hoang et al. |
| 2007/0130707 A1 | 6/2007 | Cohen et al. |
| 2007/0157408 A1 | 7/2007 | Bargiel et al. |
| 2007/0225660 A1 * | 9/2007 | Lynn ..................... 604/265 |
| 2007/0266509 A1 | 11/2007 | Kohlruss et al. |
| 2007/0277852 A1 | 12/2007 | Condliff |
| 2007/0282280 A1 | 12/2007 | Tennican |
| 2008/0011310 A1 | 1/2008 | Anderson et al. |
| 2008/0014224 A1 | 1/2008 | Boyd et al. |
| 2008/0019889 A1 | 1/2008 | Rogers et al. |
| 2008/0033371 A1 | 2/2008 | Updegraff et al. |
| 2008/0038167 A1 | 2/2008 | Lynn |
| 2008/0039803 A1 | 2/2008 | Lynn |
| 2008/0086091 A1 | 4/2008 | Anderson et al. |
| 2008/0098543 A1 | 5/2008 | Esquenet et al. |
| 2008/0103210 A1 | 5/2008 | Shapiro |
| 2008/0132880 A1 | 6/2008 | Buchman |
| 2008/0137969 A1 | 6/2008 | Rueckert et al. |
| 2008/0138438 A1 | 6/2008 | Taylor et al. |
| 2008/0147047 A1 | 6/2008 | Davis et al. |
| 2008/0152894 A1 | 6/2008 | Beihoffer et al. |
| 2008/0172007 A1 | 7/2008 | Bousquet |
| 2008/0177250 A1 | 7/2008 | Howlett et al. |
| 2008/0187460 A1 | 8/2008 | Utterberg et al. |
| 2008/0194994 A1 | 8/2008 | Brown et al. |
| 2009/0028750 A1 | 1/2009 | Ryan |
| 2009/0062766 A1 | 3/2009 | Howlett et al. |
| 2009/0099529 A1 | 4/2009 | Anderson et al. |
| 2009/0104281 A1 | 4/2009 | Taylor et al. |
| 2009/0117164 A1 | 5/2009 | Toreki et al. |
| 2009/0126134 A1 | 5/2009 | Whipple et al. |
| 2009/0137969 A1 | 5/2009 | Colantonio et al. |
| 2009/0143470 A1 | 6/2009 | Hoang et al. |
| 2009/0162301 A1 | 6/2009 | Tarrand |
| 2009/0165228 A1 | 7/2009 | Kilkenny et al. |
| 2009/0175759 A1 | 7/2009 | Davis et al. |
| 2009/0191249 A1 | 7/2009 | Adelakun |
| 2009/0205151 A1 | 8/2009 | Fisher et al. |
| 2009/0241991 A1 | 10/2009 | Vaillancourt et al. |
| 2010/0050351 A1 | 3/2010 | Colantonio et al. |
| 2010/0083452 A1 | 4/2010 | Vaillancourt et al. |
| 2010/0200017 A1 | 8/2010 | Kerr et al. |
| 2011/0030726 A1 | 2/2011 | Vaillancourt et al. |

FOREIGN PATENT DOCUMENTS

| | | |
|---|---|---|
| DE | 10 2005 027 982 A1 | 12/2006 |
| EP | 1977714 A1 | 10/2008 |
| JP | 2003 319825 | 11/2003 |
| JP | 2008094915 A | 4/2008 |

| | | |
|---|---|---|
| WO | WO 99/04623 | 2/1999 |
| WO | 0015036 A1 | 3/2000 |
| WO | 2004018003 A1 | 3/2004 |
| WO | 2004084973 A2 | 10/2004 |
| WO | 2006019782 A2 | 2/2006 |
| WO | WO 2006/019782 A2 | 2/2006 |
| WO | 2006062846 A2 | 6/2006 |
| WO | 2006138111 A1 | 12/2006 |
| WO | 2007084908 A2 | 7/2007 |
| WO | 2007097985 A2 | 8/2007 |
| WO | 2007137056 A2 | 11/2007 |
| WO | 2008100950 A2 | 8/2008 |
| WO | 2009123709 A2 | 10/2009 |
| WO | 2010039171 A1 | 4/2010 |
| WO | 2011022601 A1 | 2/2011 |

OTHER PUBLICATIONS

PCT/US2009/002011 filed Mar. 30, 2009 Search Report dated Jun. 1, 2009.
PCT/US2009/002011 filed Mar. 30, 2009 Written Opinion dated Jun. 1, 2009.
PCT/US2009/005120 filed Sep. 14, 2009 Search Report dated Jul. 1, 2010.
PCT/US2010/029641 filed Apr. 1, 2010 Search Report dated Jul. 1, 2010.
PCT/US2010/029641 filed Apr. 1, 2010 Written Opinion dated Jul. 1, 2010.
U.S. Appl. No. 12/584,740, filed Sep. 11, 2009 Non-Final Office Action mailed Jul. 27, 2010.
U.S. Appl. No. 60/832,437, filed Jul. 21, 2006 entitled Disinfecting Cap.
U.S. Appl. No. 60/850,438, filed Oct. 10, 2006 entitled Disinfecting Cap.
U.S. Appl. No. 61/195,002, filed Oct. 2, 2008 entitled Site Scrub Brush.
U.S. Appl. No. 11/281,711, filed Nov. 17, 2005 Final Office Action dated Jun. 11, 2010.
U.S. Appl. No. 11/705,805, filed Feb. 12, 2007 Non-Final Office Action mailed Sep. 22, 2009.
U.S. Appl. No. 11/705,805, filed Feb. 12, 2007 Notice of Allowance mailed Jun. 21, 2010.
U.S. Appl. No. 12/079,965, filed Mar. 31, 2008 Final Office Action dated Mar. 5, 2010.
U.S. Appl. No. 12/079,965, filed Mar. 31, 2008 Non-Final Office Action dated Oct. 2, 2009.
PCT/US2009/002011 filed Mar. 30, 2009 International Preliminary Report on Patentability dated Oct. 5, 2010.
PCT/US2009/005120 filed Sep. 14, 2009 Written Opinion dated Jul. 1, 2010.
PCT/US2010/046096 filed Aug. 20, 2010 Search Report dated Oct. 1, 2010.
PCT/US2010/046096 filed Aug. 20, 2010 Written Opinion dated Oct. 1, 2010.
U.S. Appl. No. 12/584,740, filed Sep. 11, 2009 Final Office Action dated Feb. 17, 2011.
U.S. Appl. No. 12/079,965, filed Mar. 31, 2008 Non-Final Office Action dated Mar. 9, 2011.
PCT/US2009/005120 filed Sep. 14, 2009 Preliminary Report on Patentability dated Apr. 5, 2011.
U.S. Appl. No. 12/584,740 filed Sep. 11, 2009 Notice of Allowance dated Jun. 21, 2011.

* cited by examiner

MICROBIAL SCRUB BRUSH

This invention relates to a microbial scrub brush. More particularly, this invention relates to a microbial scrub brush for a female luer and any female luer type connector including a swabable valve connector.

As is known, in a normal hospital atmosphere, female luers are used on catheters and extension line sets for drug delivery and IV infusions. Many times, a catheter will be placed in a patient and an extension line attached to the catheter for the delivery of fluids to the patient via the catheter. Generally, over time, the extension line set requires replacement with a fresh extension line set. When this is required, a current procedure is to first remove the extension line set from the catheter. Next, the existing female catheter hub on the catheter is wiped with an alcohol prep pad to clean the contact surfaces of the female luer. Thereafter, a fresh extension line set is connected to the female luer.

If the female luer is not fully cleaned, the rate of infection increases. The same is true for connecting and disconnecting on the extension line set at different points of entry, for example, a connection at a needle-less connector.

At the present time, there is no known product on the market that specifically addresses the cleaning of the female luer prior to reconnection of a new sterile extension line set.

Accordingly, it is an object of the invention to provide a simple economical device for disinfecting a female luer to receive an extension set.

It is another object of the invention to provide a sterile device to clean a female luer or any similar swabable luer.

It is another object of the invention to provide a relatively simple sterile single use device to disinfect a female luer during connection of an extension set.

Briefly, the invention employs a swab in the form of a piece of foam material that is impregnated with an anti-bacterial disinfectant and into which a female luer or the like may be inserted for cleaning upon rotation of the piece of foam material about the luer.

In addition, the swab is disposed within a housing that allows a user to manipulate the swab using the fingers of a hand. In this respect, the swab is secured, for example, by an adhesive, within the housing so that after insertion of a female luer into the swab, the housing and, thus, the swab can be rotated by the user about the surfaces of the luer. The housing is also provided with indicia to indicate to the user the number of full turns of the housing about a luer when in use.

After securement of the swab in the housing, a removable lid is placed on the housing in order to maintain the sterility of the swab prior to use.

In particular, the invention provides a microbial scrub brush that is comprised of a housing that defines a cavity, an insert of foam material that is disposed in the cavity and an anti-bacterial disinfectant in the insert.

The housing is sized to be readily handled using two or three fingers of a hand. Further, the housing is sized so that a female luer may be readily inserted into the insert within the housing cavity.

In one embodiment, the insert is provided with an annular portion for enveloping an outer surface of the female luer as well as a central portion for insertion within a central passage of the female luer for sterilizing an interior of the female luer.

The insert of foam material may be of any suitable material such as a semi-closed hydrophilic polyurethane medical grade foam. The foam material may also be a closed foam, an open foam or a semi-closed foam.

The anti-bacterial disinfectant may be of any suitable type and is in any suitable amount depending upon the size of the insert of foam material. For example, use is made of an aqueous solution containing 2% chlorhexidine gluconate (chlorhexidine Solution) in an amount of from 0.20 cc to 0.75 cc, and preferably 0.50 cc.

The scrub brush is also provided with a lid to seal the cavity and insert from the surrounding environment and to maintain the insert within the housing in a sterile condition and to keep the insert from drying out. The lid may also be provided with a pull tab to facilitate removal of the lid from the housing when the brush is to be used.

In normal operations, the lid is removed from the brush in order to expose the end of the insert within the housing. The brush is then placed over an exposed female luer, i.e. a needle-less connector, and rotated, for example for two complete revolutions. While rotating, the brush will self thread onto the female luer until the luer bottoms out. After completion, for example, of two full rotations, the brush can be removed from the luer by sliding the brush off the luer and discarded according to standard hospital protocol.

These and other objects and advantages of the invention will become more apparent from the following detailed description taken in conjunction with the accompanying drawings wherein.

Figure 1:
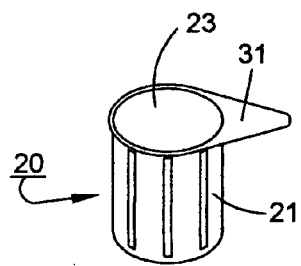
FIG. 1 illustrates a perspective view of microbial scrub brush in accordance with the invention.
Figure 2:
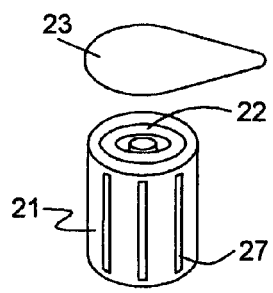
FIG. 2 illustrates an exploded view of the scrub brush of FIG. 1.

Referring to FIGS. 1 and 2, the microbial scrub brush 20 is comprised of a housing 21, a swab in the form of an insert 22 and a lid 23.

Figure 4:
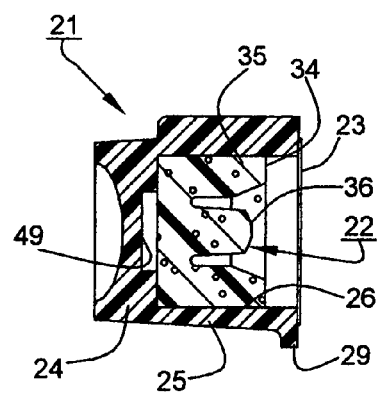
FIG. 4 illustrates a cross-sectional view of the scrub brush of FIG. 1.
Figure 3:
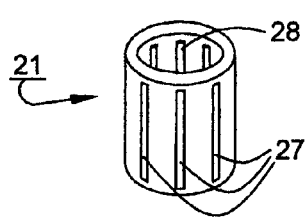
FIG. 3 illustrates a perspective view of the housing of the scrub brush of FIG. 2.

Referring to FIGS. 3 and 4, the housing 21 is of one piece in a cup shape and is formed of a base 24 and a ring 25 integral with the base 24 to define a cavity 26 of cylindrical shape with an open end. The housing 21 is made by injection molding and is made of an alcohol compatible material, such as polypropylene.

As indicated in FIG. 4, the cavity 26 is coaxial of the longitudinal axis of the housing 21. The overall dimensions of the housing 21 are such that the housing 21 may be readily handled and rotated using two or three fingers of a hand. For example, the housing 21 may have an outside diameter of 0.725 inches and a length of 0.650 inches.

Referring to FIG. 3, the housing 21 has a plurality of ribs 27 of the exterior surface of the ring 25 to provide a gripping surface. Any other suitable type of knurling may also be used. The housing 21 may also contain a plurality of ribs 28 on the interior surface of the ring 25 that extend into the cavity 26 in order to engage the insert 22 (not shown) to prevent the insert 22 from rotating within the cavity 17.

Alternatively, the insert 22 may be adhesively secured against rotation within the housing 21.

Referring to FIG. 4, the housing 21 is provided with an indicia, for example in a form of a projecting index bar 29, on the exterior surface in order to indicate a degree of rotation of the housing 21 when in use and, particularly, the number of rotations that the brush 20 is turned during use.

Figure 5:
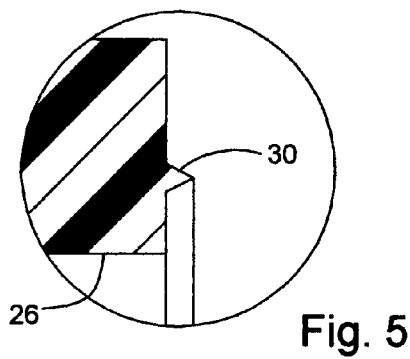
FIG. 5 illustrates a detailed view of a surface of the housing of FIG. 4.

Referring to FIG. 5, the housing 21 has an annular boss 30 at one end concentric to the cavity 26 for heat sealing of the lid 23 thereon. In this respect, the lid 23 is a die-cut foil lid that is coated with a material that readily heat seals to the polypropylene housing 21 via the boss 30. As indicated in FIG. 1, the lid 23 is provided with a pull tab 31 that extends therefrom and from the housing 21 in order to facilitate manual removal of the lid 23 from the housing 21.

Figure 6:
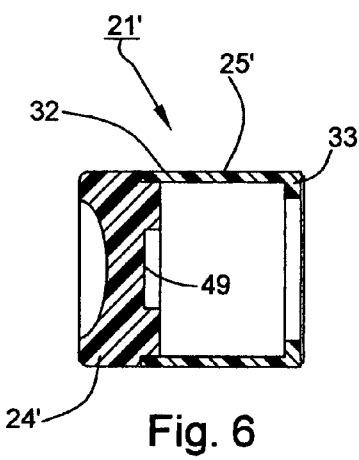
FIG. 6 illustrates a cross-sectional view of a modified housing in accordance with the invention.

Referring to FIG. 6, wherein like reference character indicate like parts as above, the housing 21' may also be made in a two-piece construction. For example, the housing 21' includes a base 24' that receives a ring 25' in a fixed relation. As indicated, the base 24' has a shouldered annular portion 32 that receives the ring 25' in a recessed manner so that a smooth outer surface is presented by the base 24' and ring 25'.

In addition, the ring 25' is provided with an inwardly directed lip 33 at an end opposite the base 24' in order to retain an insert 22 (not shown) therein.

Figure 7:
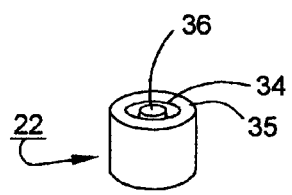
FIG. 7 illustrates a perspective view of the insert of the scrub brush of FIG. 2.

Referring to FIGS. 4 and 7, the insert 22 is a foam material, for example, of injection molded construction or the insert 22 may be die-cut from a foam sheet. The insert 22 is mounted in the housing 21 to be exposed to the open end of the housing 21.

The distal end 34 of the insert 22 is flat and slightly recessed within the open end of the housing 21 and the proximal end of the insert 22 is flat and can be secured by way of a suitable adhesive onto the base 24 of the housing 21. Typically, the insert 22 has an outer diameter of 9/16 inch (0.5625 inches).

The insert 22 includes an annular portion 35 and a central portion 36 with a flat end within the annular portion 35. The flat end of the central portion 36 may be co-planar with the end of the annular portion 35 as indicated in FIG. 7 or may be recessed within the annular portion 35 as indicated in FIGS. 4 and 8.

Figure 8:
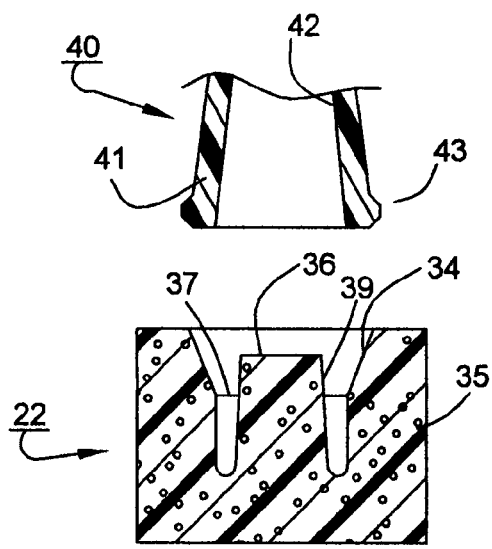
FIG. 8 illustrates a view of a female luer being inserted into the insert of the scrub brush in accordance with the invention.

As illustrated in FIG. 8, the insert two portions 35, 36 are circumferentially spaced apart to define an annular gap 37 therebetween. In addition, the annular portion 35 has a conical inwardly directed surface 38 that provides a narrowing entrance to the gap 37 for a female luer 40 while the central portion 36 has an outer conical surface 39 that is formed with a 6% taper for engagement with the taper of the female luer 40.

The exterior of the insert 22 may be formed to match and interlock with the internal ribs 28 of the housing 21 (see FIG. 3) to prevent rotation of the insert 22 within the housing 21.

The insert 22 is made of a semi-closed cell, hydrophilic polyurethane medical grade foam with a moderate absorption rate. The foam configuration and size is such as to hold 0.5 cc of an anti-bacterial solution with no solution leak-out.

During assembly of the scrub brush 20, the insert 22 is first secured within the housing 21 and then impregnated with the anti-bacterial solution. Thereafter, the lid 23 is secured to the housing 21.

Referring to FIG. 8, the insert 22 is sized to be used with a female luer 40 having an outer peripheral surface 41, a central passage 42 and a flange 43 about the passage 42. As indicated, the annular portion 35 of the insert 22 is sized to envelope and wipe the outer surface 41 of the female luer 40 and the central portion 36 is sized to move into the passage 42 of the female luer 40 for wiping the passage 42.

In normal operation, the lid 23 is removed to expose the insert 22 and the brush 20 is placed over the female luer 40 with the luer 40 inserted into the gap 37 between the two portions 35, 36 of the insert 22. The conical entrance portion 38 of the insert 22 facilitates centering of the brush 20 on the luer 40.

Next, the brush 20 is rotated. The rotation of the brush 20 causes a self-threading of the insert 22 into the passage 42 of the luer 40 until the luer 40 bottoms at the base of the gap 37 defined by the annular portion 35 and the central portion 36 of the insert 22. Typically, the brush 20 is rotated 360° twice. Upon completion of two full rotations, the brush 20 can be removed by sliding the brush 20 off the luer 40 and discarded.

The housing 21 of the scrub brush 20, when sealed by the lid 23, protects against drying out of the insert 22 and after removal of the lid 23 serves as a convenient holder for wiping of the insert 22 about a female luer or the like.

Figure 9:
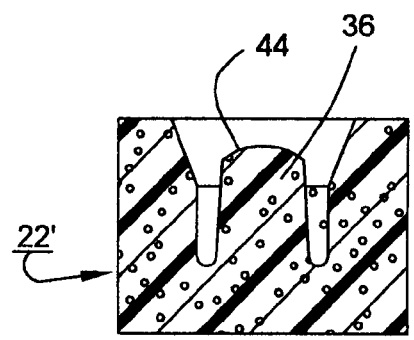
FIG. 9 illustrates a cross-sectional view of a modified insert in accordance with the invention.

Referring to FIG. 9, wherein like reference characters indicate like parts as above, the central portion 36 of the insert 22' may be provided with a rounded end or crown 44 rather than a flat surface as indicated in FIG. 8. The rounded crown 44 is particularly useful where the scrub brush 20 is used to clean a swabable luer having a flat end or the like (not shown). In this case, the peak of the crown 44 would first contact the flat end of the swabable luer in a point-to-point manner. Then, as the brush 20 is further pushed against the luer, the crown 44 would compress thereby compressing the central portion 36 of the insert 22'. As the brush is then rotated, a scrubbing action takes place between the surface of the now compressed central portion 36 and the luer surface.

Figure 10:
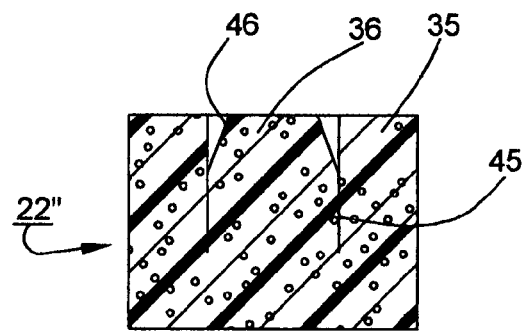
FIG. 10 illustrates a cross-sectional view of a further modified insert in accordance with the invention.

Referring to FIG. 10, wherein like reference characters indicate like parts as above, the insert 22" may be constructed without a gap between the annular portion 35 and central portion 36. In this embodiment, the two portions 35, 36 are contiguous to each other and define a slit 45 rather than a gap for receiving a luer. Further, the central portion 36 is co-extensive with the annular portion 35, i.e. the central portion 36 is not recessed, and is provided with a conically tapered surface 46 at the entrance end to the slit 45 to provide a small gap with the annular portion 35.

Figure 11:
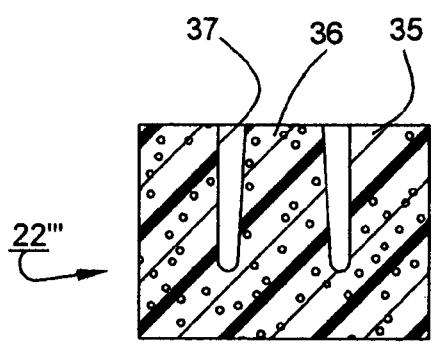
FIG. 11 illustrates a cross-sectional view of a further modified insert in accordance with the invention.

Referring to FIG. 11, wherein like reference characters indicate like parts as above, the insert 22''' may be constructed with an annular gap 37 between the annular portion 35 and central portion 36 that extends for the full depth of the central portion 36 without a conical entrance portion as in FIG. 8.

Figure 12:
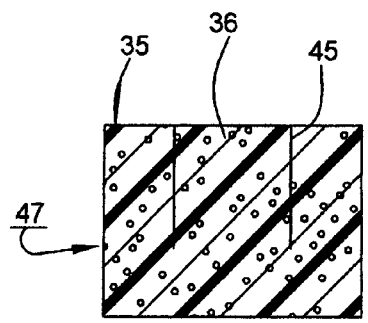
FIG. 12 illustrates a cross-sectional view of an insert that is die cut in accordance with the invention.
Figure 13:
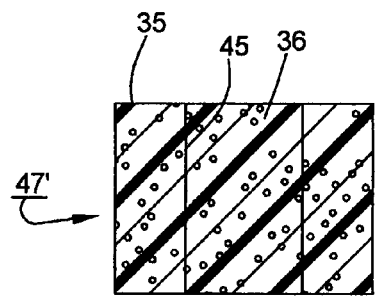
FIG. 13 illustrates a cross-sectional view of a modified die-cut insert in accordance with the invention.
Figure 14:
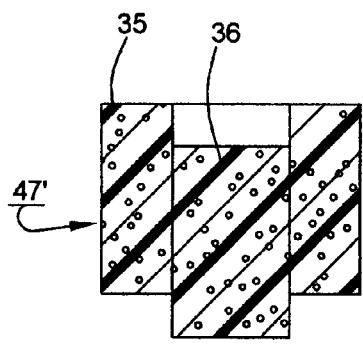
FIG. 14 illustrates a cross-sectional view of a further modified die-cut insert in accordance with the invention.

Referring to FIG. 12, wherein like reference characters indicate like parts as above, the insert 47 is die cut to form a slit 45 with the two portions 35, 36 contiguous to each other. As illustrated, the slit 45 extends from the face of the insert 47 and terminates short of the rear end of the insert 47. Alternatively, the slit 45 may extend completely through the insert 47' as shown in FIG. 13. Also, the central portion 36 may be pushed relative to the annular portion 35 so as to extend beyond the annular portion 36 as shown in FIG. 14. In this latter case, the exposed rear end 48 of the central portion 36 may extend into a recess 49 formed in the base 24 of the housing 21 (see FIG. 4) and be secured therein by an adhesive.

Figure 15:
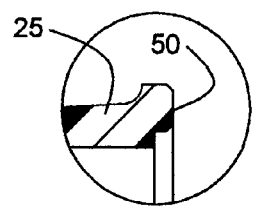
FIG. 15 illustrates a modified surface on the housing for receiving a closure lid.

Referring to FIG. 15, wherein like reference characters indicate like parts as above, the housing ring 25 may be formed with a flat surface 50 that is textured in order to receive an adhesive for securing the lid 23 (see FIG. 4) in place or the lid 23 may be heat sealed in place.

Figure 17:
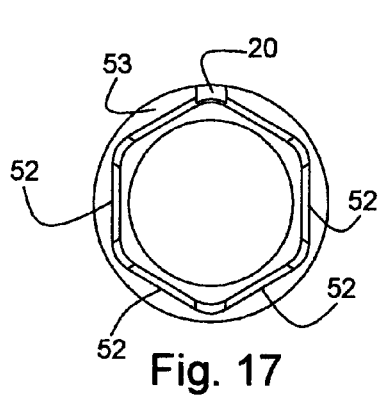
FIG. 17 illustrates a rear closed end view of the housing of FIG. 16.
Figure 16:
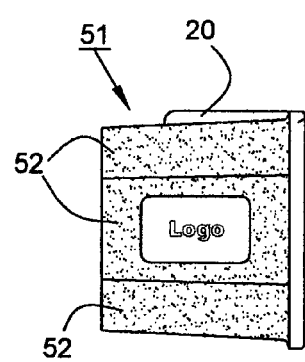
FIG. 16 illustrates a side view of a modified housing in accordance with the invention.
Figure 18:
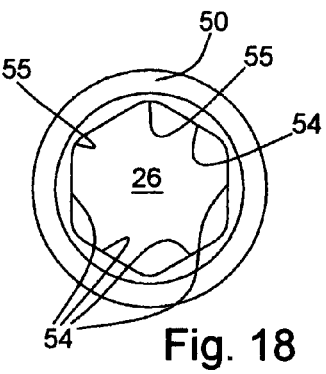
FIG. 18 illustrates a front open end view of the housing of FIG. 16.

Referring to FIGS. 16 to 18, wherein like reference characters indicate like parts as above, the housing 51 may be made with a polygonal outer cross-section, such as a hexagonal cross-section, to provide a plurality of contiguous flat surfaces 52 for easier gripping by the fingers of a user's hand. These surfaces 52 may be textured or roughened to facilitate gripping. Also, one or more of the flat surfaces may be provided with indicia, such as a logo of the manufacturer or the like.

The housing 51 has a short flange 53 at the open end that is also provided to form a surface 50 for receiving a lid 23 as described above.

In addition, the housing 51 has a cavity 26 that is of a polygonal shape complementary to the outer cross-section to provide a plurality of flat walls 54. The cavity 26 and walls 54 are sized to receive the insert 22 in a compressed condition. That is, for a cylindrical insert 22 of 9/16 inch diameter, the oppositely disposed walls 54 are spaced apart by 0.500 inches and the oppositely disposed corners 55 formed by the walls 54 are spaced apart 0.553 inches. The insert 22 is, thus, circumferentially compressed within the cavity 26.

When a luer is inserted into the insert 22 in the housing 51, the degree of compression imposed upon the insert 22 when placed in the housing 51 causes the insert to wipe the surfaces of the luer with a scrubbing action.

The scrub brush 20 may be modified in various manners. For example, where the device being cleaned does not have a central passage, the insert 22 of the scrub brush 20 may be made without a central portion 36. In this embodiment, the scrub brush would be placed over the end of the device and then rotated so as to thread the scrub brush onto the end of the device for disinfecting purposes. Also, in this embodiment, having the insert mounted in the housing in a circumferentially compressed manner would facilitate the disinfecting action of the scrub brush on the device.

The invention thus provides a device that is easily handled and that is able to disinfect a female luer in an easy manner. Further, invention provides a device that is able to disinfect the interior of a female luer. This is a particular advantage over a cloth type wipe that cannot be readily inserted into the passage of a female luer.

The invention further provides an insert that is impregnated with an anti-bacterial solution for decontamination of a luer site that is contained in a sterile condition until ready for use and that can be readily manipulated when in use.

What is claimed is:

1. A microbial scrub brush, comprising:
    a cup-shaped housing defining a cavity and having an open end;
    a swab of foam material disposed in said cavity and exposed to said open end of said housing, said swab including a central portion concentrically within an annular portion, the central portion insertable into a central passage of a female luer, wherein the annular portion, comprising a conical inwardly directed surface, is radially separated from the central portion, comprising an outer conical surface, by a circumferential slit; and
    an anti-bacterial disinfectant in said swab.

2. A microbial scrub brush as set forth in claim 1, wherein said housing is of cylindrical shape about a longitudinal axis and said cavity is of cylindrical shape and coaxial of said axis.

3. A microbial scrub brush as set forth in claim 2, wherein said housing is of one-piece.

4. A microbial scrub brush as set forth in claim 2, wherein said housing includes a base and a ring secured to and extending from said base to define said cavity.

5. A microbial scrub brush as set forth in claim 2, wherein said housing has a plurality of ribs radially directed into said cavity and engaging said swab to prevent said swab from rotating within said cavity.

6. A microbial scrub brush as set forth in claim 1, further comprising a lid removably mounted on said housing for sealing over said cavity and said swab.

7. A microbial scrub brush as set forth in claim 1, wherein said swab includes said annular portion for enveloping an outer surface of a female luer.

8. A microbial scrub brush as set forth in claim 1, wherein said swab is made in one-piece.

9. A microbial scrub brush as set forth in claim 1, wherein said swab is a semi-closed hydrophilic polyurethane medical grade foam.

10. A microbial scrub brush as set forth in claim 1, wherein said disinfectant is in an amount of 0.5 cc.

11. A microbial scrub brush as set forth in claim 1, wherein said cavity of said housing is of polygonal cross-section shape and said swab is circumferentially compressed within said cavity.

12. A microbial scrub brush as set forth in claim 11, wherein said housing has on outer polygonal cross-sectional shape to define a plurality of flat surfaces.

13. A microbial scrub brush as set forth in claim 12, wherein each of said flat surfaces has a textured surface for gripping.

* * * * *